United States Patent [19]

Tiller et al.

[11] Patent Number: 5,702,780
[45] Date of Patent: Dec. 30, 1997

[54] SCENTED ROCK AND METHOD FOR MAKING THE SAME

[76] Inventors: Norman Andrew Tiller, 452 Kinghorn Dr., Nampa, Id. 83651; Louis George Grundel, 810 I St., Rupert, Id. 83350

[21] Appl. No.: 546,479

[22] Filed: Oct. 20, 1995

[51] Int. Cl.$^6$ ................. B32B 5/16; C14C 9/00
[52] U.S. Cl. ............. 428/15; 63/DIG. 2; 428/402; 428/540
[58] Field of Search ............. 428/403, 540, 428/15, 402; 512/4; 63/DIG. 2

[56] References Cited

U.S. PATENT DOCUMENTS

| | | | |
|---|---|---|---|
| 195,324 | 3/1877 | Atkinson | 63/23 |
| 3,953,378 | 4/1976 | Lasser | 106/778 |
| 3,955,314 | 5/1976 | Robb | 46/193 |
| 4,040,619 | 8/1977 | Landi | 272/68 |
| 4,254,179 | 3/1981 | Carson, III et al. | 428/311 |
| 4,411,855 | 10/1983 | Fiebig et al. | 264/219 |
| 4,419,395 | 12/1983 | Sugimoto | 428/28 |
| 4,517,308 | 5/1985 | Ehlenz et al. | 502/401 |
| 4,657,021 | 4/1987 | Perry et al. | 128/630 |
| 4,788,164 | 11/1988 | Che et al. | 501/39 |
| 4,929,211 | 5/1990 | Resnick et al. | 446/14 |
| 4,957,787 | 9/1990 | Reinhardt et al. | 428/24 |
| 5,037,343 | 8/1991 | Benites | 446/268 |
| 5,071,704 | 12/1991 | Fischel-Ghodsian | 428/354 |
| 5,233,371 | 8/1993 | Guillet | 351/111 |
| 5,334,581 | 8/1994 | Behan et al. | 512/2 |

*Primary Examiner*—H. Thi Le
*Attorney, Agent, or Firm*—Frank J. Dykas

[57] ABSTRACT

A method for impregnating rock or mineral with scented and/or colored fluid. To impregnate the rock or mineral with scented fluid, the rock or mineral is heated to dehydrate it, and cooled to an ambient temperature in a dehumidified chamber, and then placed in a pressurizable container which is filled with scented fluid. The pressurizable container is placed under pressure for a sufficient time that the scented fluid is forced into the interstices of the rock or mineral. When the rock or mineral is removed from the pressurizable container, it has been impregnated with scented fluid and emits a pleasant odor. The rock or mineral may be cleaned using water or a solvent.

14 Claims, 3 Drawing Sheets

SCENTED ROCK AND METHOD FOR MAKING THE SAME

BACKGROUND OF THE INVENTION

1. Technical Field

This invention generally relates to a method of making scented and/or dyed rocks, and more particularly to a process for impregnating rock with a permanent scent and/or color.

2. Background

Rocks, polished stones, and minerals have long been used in a variety of ways for decoration, personal adornment, interior decorating of a house, as desk-top ornamentation or paper weights, and in any number of decorative uses. Rocks, polished stones or minerals have several characteristics which add to their usefulness. They can come in an enormous range of colors, and in textures from sharp crystals to rough stones to smoothly polished stones. However, they do not have a scent, and do not emit an odor.

In the prior art, attempts have been made to provide a scented rock or other object, primarily through coating the surface of the rock. Unfortunately, this results in only a temporary scenting of the rock. The release of vapor and scent from the coating, although it may be a controlled release, is temporary at best, which results either in the loss of the scented feature, or the requirement that it be periodically renewed.

The prior art defines a mineral as a substance occurring in nature with a characteristic chemical composition and usually some type of crystal structure. The prior art defines rocks as a mixture of components of the earth's crust. Rocks can be divided into three broad categories; sedimentary, metamorphic and igneous. Sedimentary rocks are rocks which are composed of particles that were deposited in layers, often as a result of erosion and later compression. Sedimentary rocks can also include rocks made of chemicals which have been deposited by precipitation. Metamorphic rocks are sedimentary rocks which have been recrystallized by heat and pressure within the earth's crust. Igneous rocks are rocks which have been formed from a liquid state through crystallization and solidification. Each of these types of rocks has much variety in pore size. This is due to the fact that the mineral and rock grains which compose rocks vary in size and shape. Due to this fact the pore spaces in rocks also vary. Most sedimentary rocks, such as sandstone and shale, have porosities of 10 to 45%. The porosities of sedimentary rocks decrease as they become compressed and the grains cemented together. Igneous rocks are at the other extreme of the porosity scale, with unfractured granite, gabbro, and obsidian having essentially zero porosity. Metamorphic rocks, such as breccia and schist, have porosities generally less than sedimentary rocks, and more than igneous rocks. In general, a porosity of greater than 5% is regarded as low. From 5 to 15% is medium, and over 15% is considered high. Minerals such as opal and agate are composed of omorphous crystals and microcrystals, respectively, of silicon dioxide. They can contain water between the crystals, and can have a considerable percentage of water. Opal, for instance, can have up to 30% water content. In general, minerals have less porosity than sedimentary rocks, and more than most igneous rocks.

The prior art shows that the porosities of rock are often filled with water. Much of the prior art dealing with water in rocks is concerned with the water content of magma from a volcanic eruption. This interest has led scientists to devise ways to measure the water content of rocks, especially of volcanic rock. A common method is to weigh rocks before and after placing the rock in a vacuum oven, and using the difference in weight to determine how much water has been removed from the rock. These efforts in the prior art have shown that water in rocks can exist in three forms. Water can exist in large porosities of the rock as a freely drainable liquid. In smaller porosities, water also exists as a monolayer of molecules adhering to the rock surface. Due to the absorption of the water onto the rock, this mono-layer of water can be tenaciously held to the rock surface. A third form of holding water in rocks is when it is chemically bound by ionic forces or chemical bonds to chemicals within the rock itself. These water molecules are held even more tightly than absorbed water and much more tightly than drainable water. Drainable water can be removed from rock by evaporation in the air. Water which adheres in a monolayer to rock can be removed from the rock by application of heat. Application of still further heat can liberate chemically bound water from rock. Prior art has shown that the use of heat combined with vacuum is an effective way to remove water from rock pores.

The prior art shows that pores in rocks are usually connected by more or less open channels, thus providing a tortuous network of pathways through which fluids may migrate in response to a pressure gradient, or by osmotic movement of water molecules in vapor form. The rate of flow and quantity of fluid transmitted through a given cross section of rock will be related to the fluid viscosity, the size and tortuosity of the channels, which are directly related to the frictional resistance of flow, and the pressure differential.

These principles mean that moisture in rock, which can occupy from 0 to 45% of the volume of a rock, can be removed by applying heat and/or vacuum to the rock. The space in the porosities that was taken up by water can be taken up by another fluid which replaces the water. If the fluid which is to replace the water is placed under pressure, it penetrates faster into the porosities of the rock. Once in the porosities, any volatile components of the fluid would dissipate by the same mechanisms as did the water. Loosely bound chemicals would freely evaporate. Chemicals which adhere to the rock's surface will be bound more tightly to the rock and will escape more slowly.

The prior art discloses inventions which are for objects which emit odors from blocks, for squeezing liquid inside a container, for a rattle which emits an odor, for shapes which emit odors, and for coating objects with a layer of chemical which releases an odor form the object. These inventions do not cause an object to emit an odor for a very long period of time. Since coating an object with an odor places an odor-bearing chemical on the outside of the object and exposes to the atmosphere, any volatile substances in the mixture quickly evaporate into the atmosphere and leave the object odorless.

Accordingly, it is an object of this invention to provide an object made from a rock or mineral, which can be smooth or rough, which can be of a variety of shapes and colors, and has a permanent preselected odor.

A further object of the present invention is to provide a method of impregnating the rock or mineral with a scented material, such that the scented feature of the ornamental rock becomes more or less permanent.

DISCLOSURE OF INVENTION

These objects are accomplished by heating the rock or mineral for a sufficient time and at a sufficient temperature to drive away moisture. For opal, the temperature and pressure of 220° F. and 1000–1500 p.s.i. has proven effective. Other rocks or minerals would require different settings. The rock or mineral is then placed in a pressurizable container into which a scented fluid is also placed. The pressurizable container is placed under pressure, which forces the scented fluid into the interstices of the rock or mineral. After suitable time and pressure to impregnate the pores of the rock or the mineral with the scented fluid, (for opal this can be 24 hours) the pressure is released and the stone is removed. The rock or mineral is then cleaned with water or a solvent. The rock or mineral will then emit an odor and will continue to do so for a very long period of time.

BEST MODE OF THE INVENTION

Referring to FIGS. 1 through 5, the method of impregnating a rock with a scent is shown in schematic representation format. It is a process by which a hydrated or porous rock or mineral is impregnated with a scented fluid. Hydrated rocks are defined as any rock that has water bound up in it, either chemically bound or contained within the rock matrix as a liquid or as a mono-layer.

By heating the rock to drive off the unbound and loosely bound water contained within the porosities of the rock, and then replacing that water with fluid which contains a scent (volatile organic compounds), the porosities of the rock, which can be from 0 to 45%, become a reservoir of scented fluid. The scent from the fluid is gradually released through the porosities of the rock and is also bound to the surface of the rock. The scent emitted by the rock becomes more or less permanently associated with the rock.

In the preferred embodiment of the process in the Applicant's invention. The rocks or minerals are heated in a dehumidified container, at least to the boiling point of water, in order to drive off any water that may be held within. Using opal as an example, a temperature of 220° F. has proven adequate for dehydration. Again, using opal as an example, 24 hours has been sufficient time to dehydrate the opal. After heating, the rocks or minerals are cooled to ambient temperature in a chamber which is dehumidified using a dessicant.

Figure 1:
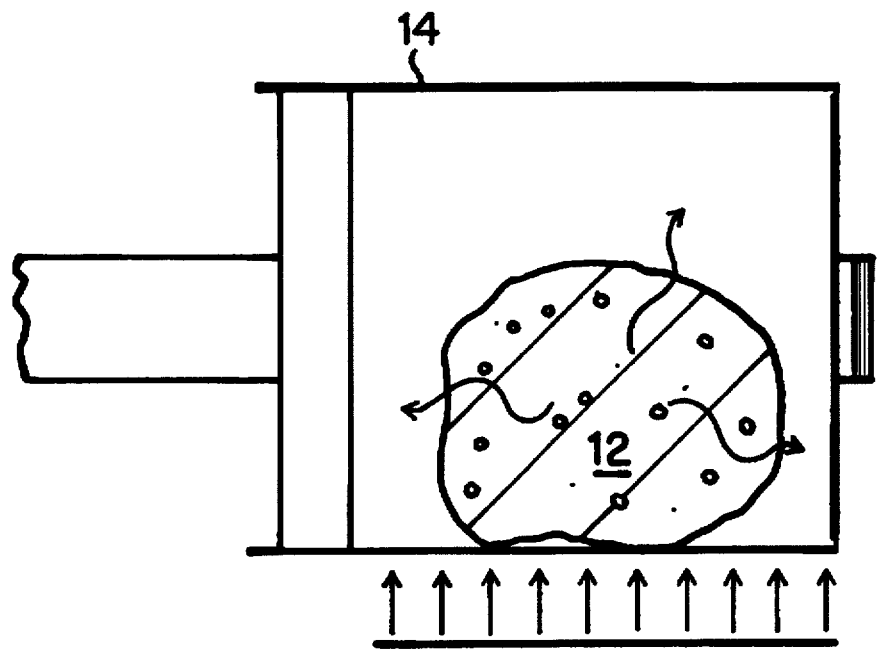
FIG. 1 is a schematic representation of a hydrated rock in a chamber to which heat is applied and water vapor from the rock is driven off.
Figure 2:
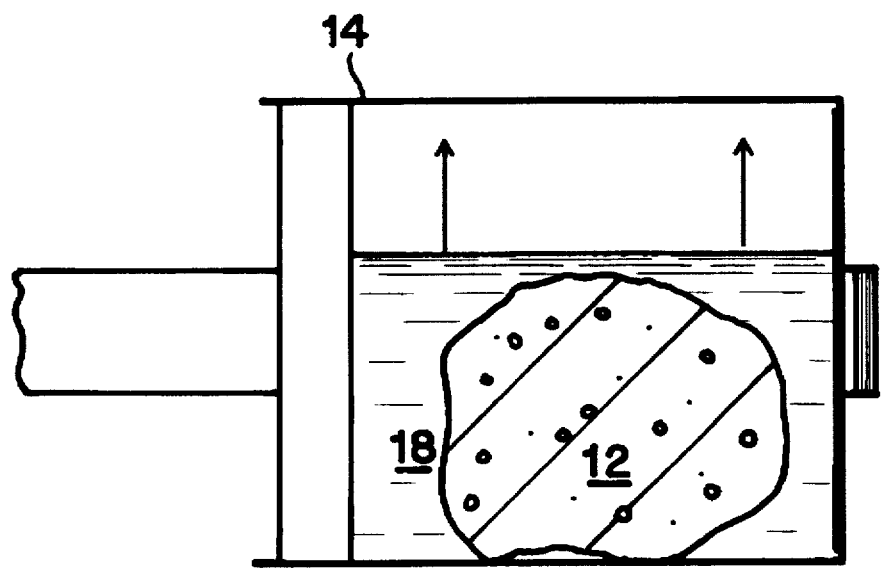
FIG. 2 is a schematic representation of the dehydrated rock immersed in a scented fluid in a pressurizable container.
Figure 3:
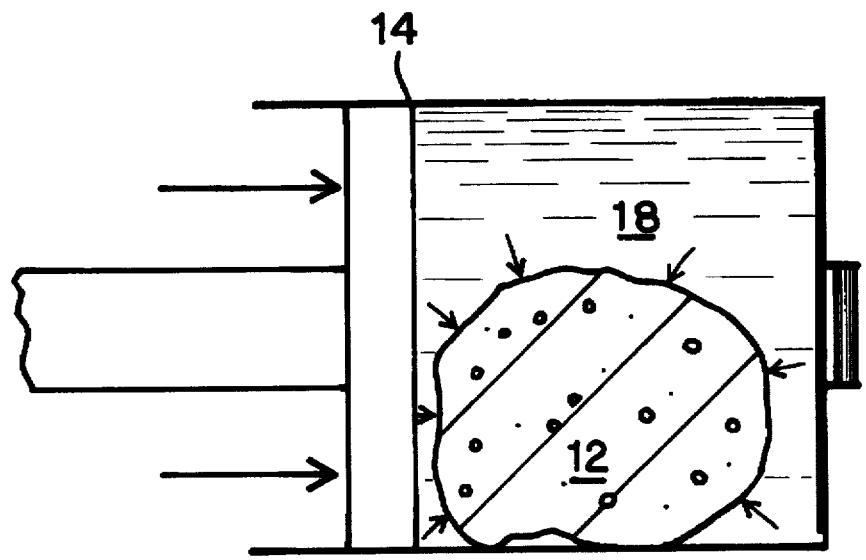
FIG. 3 is a schematic representation of the dehydrated rock immersed in scented fluid in a pressurizable container to which pressure is being applied.
Figure 4:
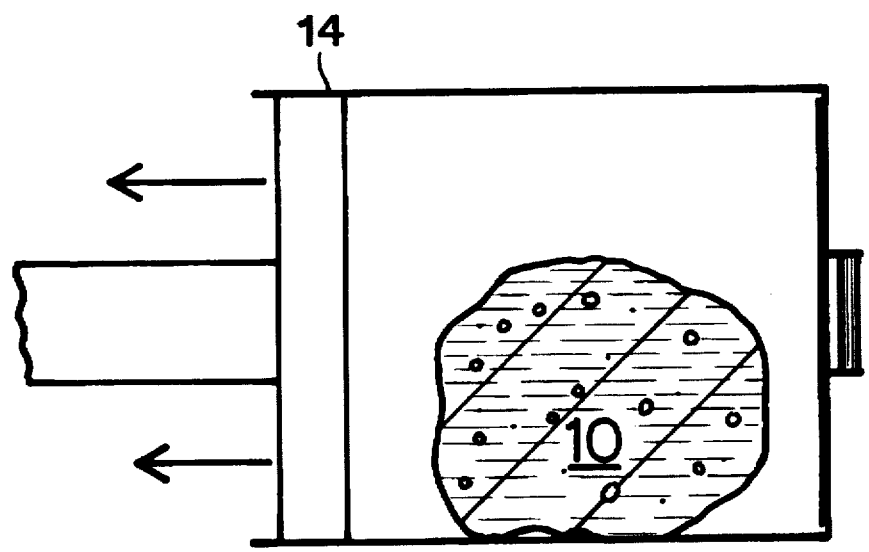
FIG. 4 is a schematic representation of a rock impregnated with a scented fluid.
Figure 5:
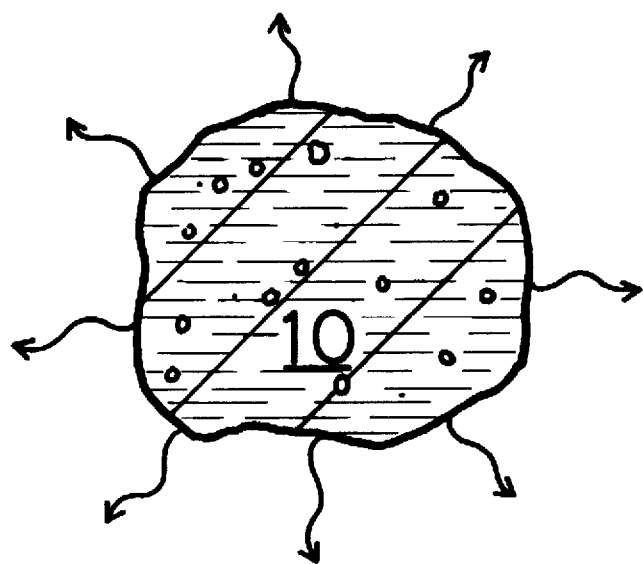
FIG. 5 shows the rock or mineral which has been impregnated with scented fluid in its final form.

The now dehydrated rock or mineral is placed in a pressurizable container (14) which is filled with a scented fluid (18). The pressurizable container is placed under pressure as shown in FIG. 3 for a preselected time and a preselected pressure to force the scented fluid into the porosities of the dehydrated rock or mineral. Using opal as an example, a pressure of 1000–1500 p.s.i. has proven suitable. After a period of time under the required pressure, the pressure is released and the remaining fluid is removed. Using opal as an example, 24 hours has proven to be a sufficient time. Using jasper, 48 hours has been required.

After the rock or mineral is removed from the vacuum chamber, it may be cleaned using water or a solvent.

While this is the preferred embodiment of the process, the process can take other forms as well. The container in which the rock or mineral is heated for dehydration can be a vacuum oven. It can also be a container made of sintered metal. The scented fluid which is impregnated under pressure into the rock or mineral matrix can be an aqueous, or water based fluid. It can also be an organic, or oil based fluid. The scented fluid which is impregnated into the rock can also contain a dye which colors the rock. This color would be exposed when the rock was sectioned and polished, or in the case of a mineral or polished rock, the color would be apparent after the pressurization step.

The rock or mineral (10), which now has been impregnated with the scented fluid, is removed from the pressurizable container. When the process is complete the rock or mineral will have several desirable attributes. It may emit a pleasant odor with a variety of possible odors to choose from. It will be of a size, shape and surface texture to make it pleasant to hold and manipulate in the hand, or it may be suitable for use in some other function typical of rocks, stones and minerals. Since the scented rock or mineral can be made from a wide variety of porous or hydrated minerals, the final product will also have the attribute of color and texture which can be used in combination with being scented. In use, the scented rock or mineral could be held in the hand and turned for relaxation, or as an aid to aromatherapy. It could be placed on a desk or counter top by itself, it could be placed in a dish, bowl, or vase with other scented stones, where it would serve as pleasant decorations for the office or home. It could be used in beaded creations; necklaces, earrings, rings and other forms of personal adornment.

While there is shown and described the present preferred embodiment of the invention, it is to be distinctly understood that this invention is not limited thereto but may be variously embodied to practice within the scope of the following claims.

We claim:

1. A method of impregnating a hydrated or porous rock or mineral with a scent, which comprises:
 (a) dehydrating the rock or mineral;
 (b) cooling the rock or mineral to an ambient temperature in a dehumidified chamber;
 (c) placing the rock or mineral in a pressurizable container;
 (d) filling the pressurizable container with a scented fluid;
 (e) pressurizing the container for a preselected period of time, and at a preselected pressure to impregnate the rock or mineral with the scented fluid;
 (f) depressurizing the container;
 (g) removing the scented rock or mineral from the pressurizable container.

2. The method of claim 1, wherein the rock or mineral is cleaned with a solvent after being removed from the vacuum.

3. The method of claim 2, wherein the solvent used to clean the rock consists of an alcohol.

4. The method of claim 3, wherein the scented fluid consists of an aqueous solution of water plus a scenting agent.

5. The method of claim 1, wherein the rock or mineral is dehydrated in a dehydrating chamber.

6. The method of claim 5, wherein the dehydration step takes place in a sintered container.

7. The method of claim 5, wherein the dehydrating chamber consists of a vacuum oven.

8. The method of claim 5, wherein the scented fluid is also colored.

9. The method of claim 1, wherein the rock or mineral is heated to approximately 220° F. to dehydrate the rock or mineral.

10. The method of claim 1, wherein the scented fluid consists of an organic solution of an oil and a scenting agent.

11. The method of claim 1, wherein a hydraulic cylinder is used to pressurize the scented fluid and rock or mineral.

12. The method of claim 1, wherein the container is pressurized to within the range of 1000 to 1500 p.s.i.

13. A method of impregnating a hydrated or porous rock or mineral having a rock or mineral matrix, with a scent which comprises:

(a) placing a rock or mineral in a container;

(b) dehydrating the rock or mineral;

(c) filling the container with a scented fluid;

(d) pressurizing the container for a preselected time and at a preselected pressure to impregnate the rock or mineral with a scented fluid;

(e) depressurizing the container;

(f) removing the rock or mineral from the container.

14. A scented rock or mineral which comprises:

a dehydrated rock or mineral having pores; and scented fluid impregnated into the pores of the rock or mineral.

* * * * *